United States Patent [19]

Newman et al.

[11] Patent Number: 5,229,411
[45] Date of Patent: Jul. 20, 1993

[54] SUBSTITUTED BENZ[CD]INDOL-2-(1H)-ONES AND USE AS ANTIHYPERTENSIVE AGENTS

[75] Inventors: Howard Newman, Monsey; Martin L. Sassiver, Spring Valley, both of N.Y.; Andrew S. Tomcufcik, Old Tappan, N.J.

[73] Assignee: American Cyanamid Company, Stamford, Conn.

[21] Appl. No.: 856,607

[22] Filed: Mar. 24, 1992

[51] Int. Cl.⁵ ............... C07D 209/90; A61K 31/40
[52] U.S. Cl. ............................ 514/411; 548/437
[58] Field of Search ............... 548/437; 514/411

[56] References Cited

U.S. PATENT DOCUMENTS

| | | | |
|---|---|---|---|
| 3,959,310 | 5/1976 | Brack et al. | 548/437 |
| 4,515,963 | 5/1985 | Begrich | 548/437 |
| 5,079,247 | 1/1992 | Tomcufcik et al. | 514/232.8 |

FOREIGN PATENT DOCUMENTS 3445252 6/1986 Fed. Rep. of Germany.

OTHER PUBLICATIONS

Mostoslavskii, Chemical Abstracts vol. 84, No. 19, Abst. No. 134,923 (1976).

*Primary Examiner*—Mary C. Lee
*Assistant Examiner*—Mary Susan H. Gabilan
*Attorney, Agent, or Firm*—Thomas S. Szatkowski

[57] ABSTRACT

Compounds of the formula:

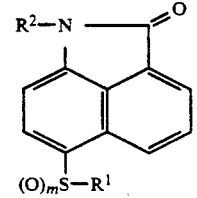

wherein $R^1$, $R^2$ and m are defined in the specification are provided. These compounds are useful as antihypertensive agents.

30 Claims, No Drawings

SUBSTITUTED BENZ[CD]INDOL-2-(1H)-ONES AND USE AS ANTIHYPERTENSIVE AGENTS

BACKGROUND OF THE INVENTION

1. Field of the Invention

This invention relates to novel benz[cd]indol-2(1H)-ones which are useful as antihypertensive agents.

2. Description of the Prior Art

In the U.S. Pat. No. 3,959,310, compounds having the formulae:

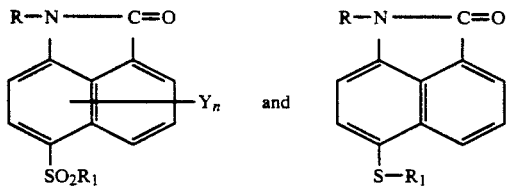

wherein:

R denotes hydrogen, an alkyl, cycloalykl, aralkyl or aryl radical or an alkyene radical bonded to the naphthalene ring in the o-position, $R_1$ denotes an alkyl, cycloalkyl, aralkyl or aryl radical or saturated or unsaturated heterocyclic radical bonded via carbon, y denotes hydrogen or a non ionic substituent and/or a carboxyl group, and n denotes the numbers 1 or 2 are disclosed as intermediates in the synthesis of cationic dyestuffs.

This patent does not disclose or suggest that such compounds have any pharmaceutical activity, particularly antihypertensive activity.

SUMMARY OF THE INVENTION

This invention provides novel compounds represented by the formula:

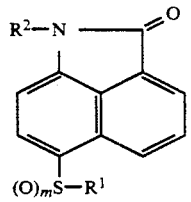

wherein $R^1$ is selected from the group consisting of lower alkyl ($C_1$-$C_4$) branched and unbranched, —CN or —$CH_2OCOR^3$ wherein $R^3$ is selected from $C_1$-$C_3$ alkyl branched and unbranched; $R^2$ is selected from the group consisting of hydrogen, lower alkyl ($C_1$-$C_4$ branched and unbranched, —$(CH_2)_qCN$, —$(CH_2)_q$-cyclopropyl, and —$COR^3$ wherein $R^3$ is selected from $C_1$-$C_3$ alkyl branched and unbranched; m is an integer from 0 to 2 and q is an integer from 1 to 3; with the provisos that when $R^1$ is —CN, m is 0 and when $R^1$ is lower alkyl, $R^2$ cannot be lower alkyl or H and when $R^2$ is lower alkyl or H, $R^1$ cannot be lower alkyl as antihypertensive agents.

In addition, the invention provides a method for using the compounds represented by the formula:

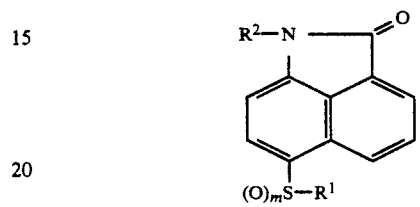

wherein $R^1$ is selected from the group consisting of lower alkyl ($C_1$-$C_4$) branched and unbranched, —CN or —$CH_2OCOR^3$ wherein $R^3$ is selected from $C_1$-$C_3$ alkyl branched or unbranched; $R^2$ is selected from hydrogen, lower alkyl ($C_1$-$C_4$) branched or unbranched, —$(CH_2)_qCN$, —$(CH_2)_q$-cyclopropyl, and —$COR^3$ wherein $R^3$ is selected from $C_1$-$C_3$ alkyl branched or unbranched; m is an integer from 0 to 2 and q is an integer from 1 to 3; with the proviso that when $R^1$ is CN, m is O as antihypertensive agents.

Finally, the invention provides a method for producing compounds of the present invention.

DETAILED DESCRIPTION OF THE INVENTION

The compounds of the present invention are prepared according to the following reaction schemes.

As shown in Scheme I, the 1,2-dihydro-2-oxobenz[cd]indol-6-yl-thiocyanic acid ester 1 is reacted with sodium borohydride in ethanol followed by alkylation with $R^4I$, where $R^4$ is lower alkyl ($C_1$-$C_4$) branched and unbranched, to afford 2. Oxidation of 2 with m-chloroperoxybenzoic acid in ethanol affords sulfoxide 3. Oxidation of 2 with hydrogen peroxide in acetic acid at reflux yields the sulfone 4. Conversion of 3 to 4 is easily accomplished using hydrogen peroxide in acetic acid at reflux. Additionally, 1 is converted to 5 by reaction with sodium borohydride in ethanol followed by the addition of bromomethylacetate.

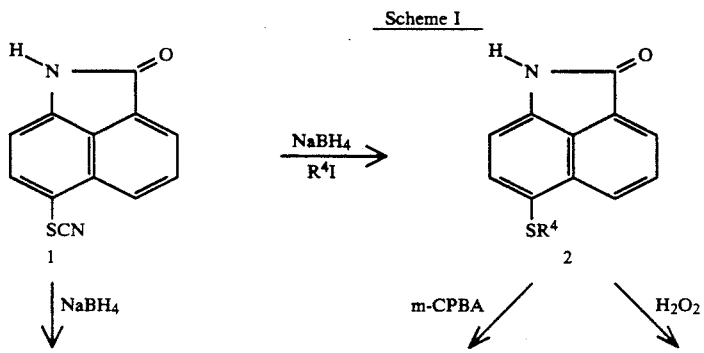

Scheme I

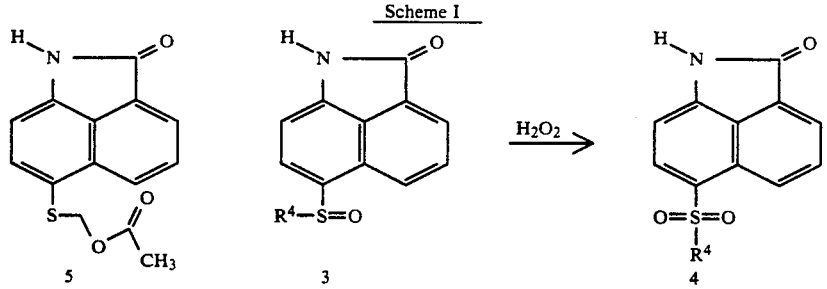

In accordance with Scheme II, 6, where $R^1$ is hereinbefore defined, is converted to 7 by reaction with sodium hydride in N,N-dimethylformamide and $R_5X$ where $R_5$ is lower alkyl ($C_1$–$C_4$), branched and unbranched, —$(CH_2)_3CN$ and —$CH_2$-cyclopropyl wherein X is bromine or iodine. Additionally, 6 is reacted with an anhydride $(R^4CO)_2O$, wherein $R_4$ is defined as lower alkyl ($C_1$–$C_4$), branched and unbranched to prepare 8. Oxidation of 8 with the proviso that $R^1$ cannot be cyano, with m-chloroperoxybenzoic acid affords sulfoxide 9. Further oxidation of 9 with hydrogen peroxide yields sulfone 10. Oxidation of 8 with the proviso that $R^1$ cannot be cyano with hydrogen peroxide affords 10. Oxidation of 7 with the proviso that $R^1$ cannot be cyano with m-chloroperoxybenzoic acid affords sulfoxide 11. Further oxidation of 11 with hydrogen peroxide yields sulfone 12. Oxidation of 7, with the proviso that $R^1$ cannot be cyano, with hydrogen peroxide also affords sulfone 12.

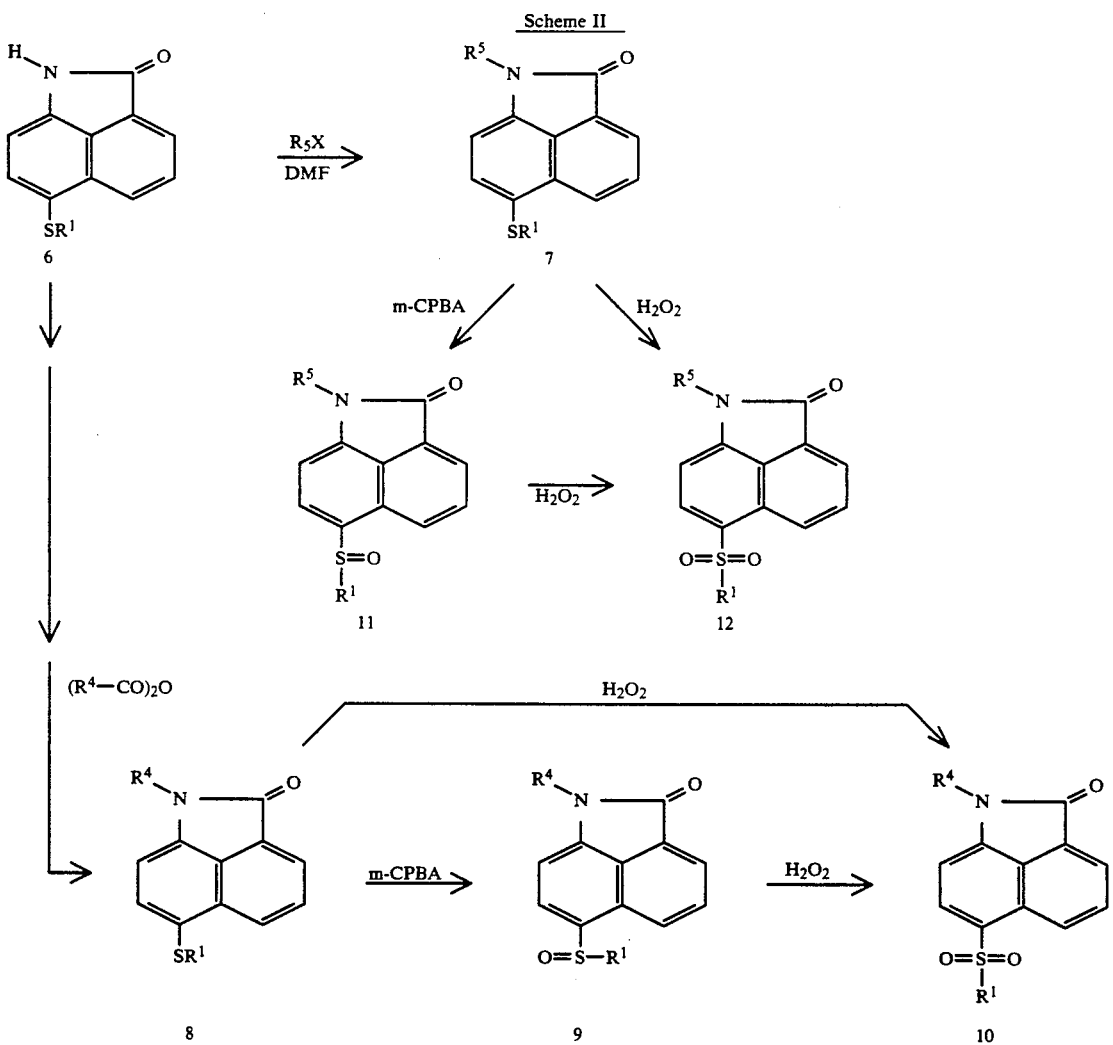

In accordance with Scheme III 3, where $R^4$ is hereinbefore defined is converted to 13 by reaction with sodium hydride in N,N-dimethylformamide and $R^5X$, where $R^5$ and X are hereinbefore defined. Additionally, 4 is converted to 14 also by reaction with sodium hydride in N,N-dimethylformamide and $R^5X$. Oxidation of 13 with hydrogen peroxide gives sulfone 14.

Scheme III

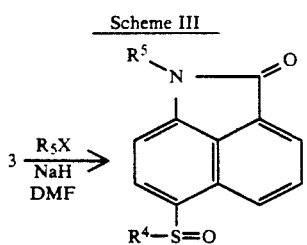

defined. Oxidation of 15 with m-chloroperoxybenzoic acid affords sulfoxide 16. Further oxidation of 16 with hydrogen peroxide yields sulfone 17. Additionally, 15 is oxidized to 17 with hydrogen peroxide. Compound 5 is acylated with $(R^4CO_2)O$, where $R^4$ is hereinbefore defined, to yield 18 which is oxidized with m-chloroperoxybenzoic acid to give sulfoxide 19. Further oxidation of 19 with hydrogen peroxide affords sulfone 20. Compound 18 is converted directly to 20 with hydrogen peroxide.

Scheme IV

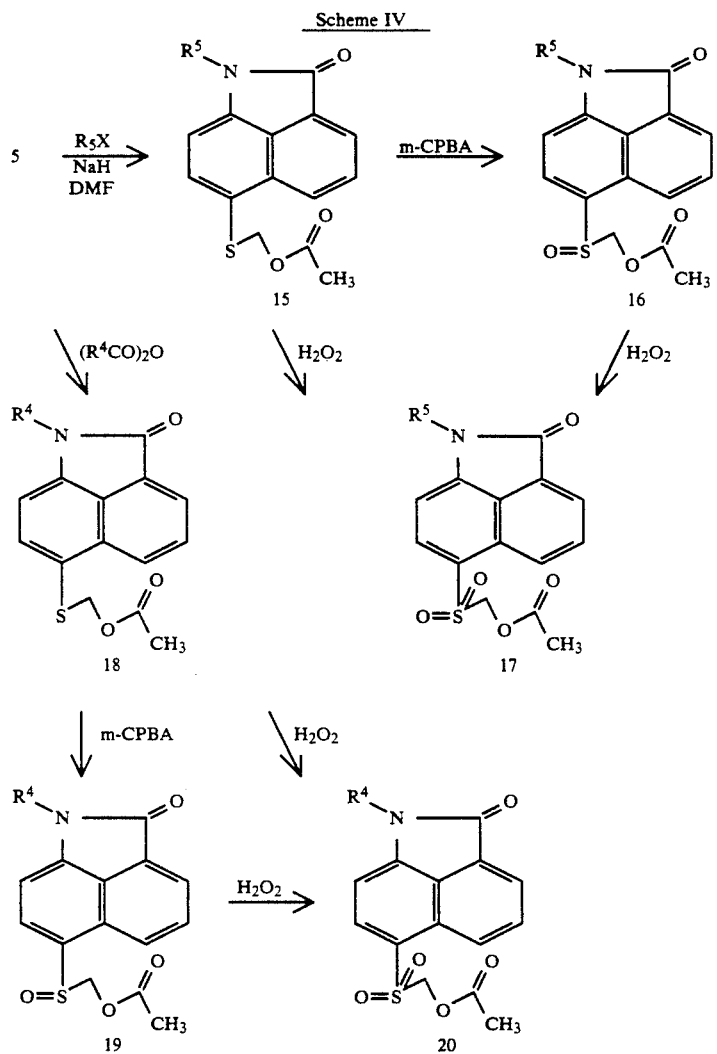

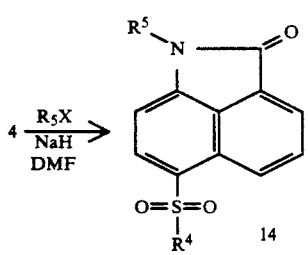

In accordance with Scheme IV, 5 is converted to 15 by reaction with sodium hydride in N,N-dimethylformamide and $R_5X$ where $R_5$ and $X$ are hereinbefore defined.

As will be appreciated in connection with the foregoing reaction schemes, preferred are those compounds as described hereinabove wherein $R^1$ is selected from the group consisting of lower alkyl ($C_1$-$C_4$) branched or unbranched, —CN or —$CH_2OCOCH_3$; $R^2$ is selected from the group consisting of hydrogen, lower alkyl ($C_1$-$C_4$) branched or unbranched, —$(CH_2)_3CN$ —$CH_2$-cyclopropyl and —$COCH_3$. Particularly preferred are those compounds as described hereinabove wherein $R^1$ is selected from the group consisting of —CN or —$CH_2OCOCH_3$ and $R^2$ is selected from the groups consisting of —$(CH_2)_3CN$, —$CH_2$-cyclopropyl and —$COCH_3$.

Hypotensive Activity in Spontaneously Hypertensive Rats

The novel compounds of the present invention are active hypotensive agents and are tested for hypotensive activity by the method of P. S. Chan and D. Poorvin, Clinical and Experimental Hypertension, 1 (6), 817–830 (1979). Male, 16 week old, spontaneously hypertensive rats of the Okamoto strain, from Taconic Farms, Germantown, N.Y., having an average mean arterial blood pressure of 160±1.5 mm of mercury, are used in the test. One to four rats are used per test compound. A rat is dosed by gavage with a test compound suspended in 2% pre-boiled starch at a concentration of 50 mg/ml, at a dose of 100 mg/kg of body weight or less, with 0.9% sodium chloride loading at a dose of 25 ml/kg of body weight. A second identical dose of the test compound, without sodium chloride loading is given 24 hours later. At 28 hours after the initial dose the mean arterial blood pressure (MABP) is measured. The procedure is repeated in a second and third rat when necessary.

The results of this test on representative compounds of the present invention appear below in Table I.

TABLE I

Hypotensive Activity

| Compound | Example # | Avg. MABP in mm Hg/HR (No. of Rats) |
|---|---|---|
| 1,2-Dihydro-2-oxobenz[cd]-indol-6-yl-thiocyanic acid ester | 1 | 99/350(2) |
| 6-(Methylthio)-benz[cd]-indol-2(1H)-one | 2 | 60/350(2) |
| 6-(Methylsulfonyl)-benz[cd]-indol-2(1H)-one | 3 | 62/370(2) |
| 1-Methyl-6-(methylsulfonyl)-benz[cd]indol-2(1H)-one | 4 | 63/290(2) |
| 1-(1-Methylethyl)-6-(methylsulfonyl)-benz[cd]indol-2(1H)-one | 5 | 119/410(2) |
| 1-(1-Methylethyl)-6-(methylthio)-benz[cd]indol-2(1H)-one | 6 | 118/430(2) |
| 1-(Cyclopropylmethyl)-6-(methylsulfonyl)-benz[cd]-indol-2(1H)-one | 7 | 121/440(2) |
| 6-(Methylthio)-2-oxo-benz[cd]indole-1(2H)-butanenitrile | 8 | 116/470(2) |
| 6-(Butylthio)-benz[cd]indol-2(1H)-one | 9 | 90/440(2) |
| 6-[(1-Methylethyl)thio]-benz[cd]indol-2(1H)-one | 10 | 109/400(2) |
| 1-Ethyl-6-(methylsulfonyl)-benz[cd]indol-2(1H)-one | 11 | 90/390(4) |
| 6-(Ethylthio)-benz[cd]indol-2(1H)-one | 12 | 50/410(2) |
| 6-(Propylthio)-benz[cd]indol-2(1H)-one | 13 | 138/520(2) |
| 1-Acetyl-6-(methylthio)-benz[cd]indol-2(1H)-one | 14 | 92/430(4) |
| 6-(Methylsulfinyl)-benz[cd]-indol-2(1H)-one | 15 | 76/430(2) |
| 1,2-Dihydro-1-methyl-2-oxo-benz[cd]indol-6-yl-thio-cyanic acid ester | 16 | 89/390(2) |
| 6-[[(Acetyloxy)methyl]thio]benz[cd]-indol-2(1H)-one | 17 | 90/340(2) |
| 6-(Ethylsulfonyl)-benz[cd]indol-2(1H)-one | 18 | 121/430(2) |
| 1-Butyl-6-(methylthio)-benz[cd]indol-2(1H)-one | 19 | 107/460(2) |
| 1-Methyl-6-(thiomethyl)-benz[cd]indol-2(1H)-one | 20 | 93/420(2) |

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as fatty oil. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

1,2-Dihydro-2-oxobenz[cd]indol-6-yl-thiocyanic acid ester

A solution of 250 ml of acetic acid containing 8 ml of acetic anhydride is refluxed for 2.5 hours then allowed to cool. Over a 10 minute period, 4 g of chlorine is bubbled through the solution. The resulting solution is treated with 5.2 g of potassium thiocyanate, in one portion, and stirred at room temperature for 30 minutes. A 8.5 g portion of benz[cd]indol-2(1H)-one is added and stirring continued for 2.5 hours. The mixture is filtered and the collected solid washed with acetic acid followed by water, air drying and vacuum drying at 60° C. for 45 minutes to afford 8.7 g of light yellow solid, m.p. 258°–262° C.

EXAMPLE 2

6-(Methylthio)-benz[cd]indol-2(1H)-one

A stirred suspension of 5.0 g of 1,2-dihydro-2-oxobenz[cd]indol-6-yl-thiocyanic acid ester (Example 1) in 75 ml of absolute ethanol is treated with 1 g of sodium borohydride with stirring for 3 hours at room temperature. A chilled solution of 1.3 g of potassium hydroxide in 15 ml of absolute ethanol is rapidly added followed by 1.5 ml of methyl iodide. After a mild exotherm, the reaction mixture is stirred at room temperature for 3 hours. The yellow solid is collected, washed with ethyl alcohol followed by water. The yellow solid is air dried then vacuum dried at 60° C. for 30 minutes to afford 3 g of yellow solid, m.p. 167°–172° C.

EXAMPLE 3

6-(Methylsulfonyl)-benz[cd]indol-2(1H)-one

A mixture of 8.87 g of 6-(methylthio)-benz[cd]indol-2(1H)-one, (Example 2) 18 ml of 30% hydrogen peroxide and 133 ml of acetic acid is heated at 125°–130° C. for one hour, then cooled. The resulting solid is collected and washed with acetic acid-water and water to afford 6.05 g of the desired product, m.p. 242°–243° C.

EXAMPLE 4

1-Methyl-6-(methylsulfonyl)-benz[cd]indol-2(1H)-one

To 25 ml of N,N-dimethylformamide is added 0.6 g of 60% sodium hydride under argon, followed by the rapid dropwise addition of a solution of 2.5 g of 6-(methylsulfonyl)-benz[cd]indol-2(1H)-one (Example 3) dissolved in 50 ml of N,N-dimethylformamide. The mixture is stirred for 20 minutes then heated at 50° C. for minutes followed by cooling to room temperature. While stirring, a solution of 2.14 g of methyl iodide in 25 ml of N,N-dimethylformamide is added dropwise. The stirring is continued at room temperature for 2 hours. The reaction mixture is poured over 200 ml of crushed ice and the resulting solid collected, washed with water and dried to afford 2.54 g of the desired product, m.p. 216°–218° C.

EXAMPLE 5

1(1-Methylethyl)-6-(methylsulfonyl)-benz[cd]indol-2(1H)-one

A mixture of 2.5 g of 6-(methylsulfonyl)-benz[cd]indol-2(1H)-one (Example 3), 0.6 g of sodium hydride and 2.7 ml of 2-bromopropane in 100 ml of N,N-dimethylformamide is reacted for 18 hours under argon using the conditions of Example 4 to yield 2.24 g of the desired product as a yellow solid, m.p. 164°–165° C.

EXAMPLE 6

1-(1-Methylethyl)-6-(methylthio)-benz[cd]indol-2(1H)-one

A mixture of 2.0 g of 6-(methylthio)-benz[cd]indol-2(1H)-one (Example 2), 0.48 g of 60% sodium hydride and 2.33 ml of 2-bromopropane in 100 ml of N,N-dimethylformamide is reacted for 23 hours using the conditions of Example 4 to yield 1.15 g of the desired product as a bright yellow solid, m.p. 70°–71° C.

EXAMPLE 7

1-(Cyclopropymethyl)-6-(methylsulfonyl)-benz[cd]indol-2(1H)-one

A mixture of 2.5 g of 6-(methylsulfonyl)-benz[cd]indol-2(1H)-one (Example 3) in 50 ml of N,N-dimethylformamide is treated with 0.35 g of sodium hydride and 1.5 ml of (bromomethyl)cyclopropane at 75° C. in a pressure bottle for 24 hours. An additional 1.5 ml of (bromomethyl)cyclopropane is added and heating continued at 75° C. for 17 hours in a pressure bottle. The reaction mixture is cooled then evaporated. The concentrate is chromatographed on silica gel using 1:1 ethyl acetate-hexane to afford 0.72 g of the desired product as yellow crystals, m.p. 148°–150° C.

EXAMPLE 8

6-(Methylthio)-2-oxo-benz[cd]indole-1(2H)-butanenitrile

A mixture of 2.15 g of 6-(methylthio)-benz-[cd]indol-2(1H)-one (Example 2), 0.6 g of 60% sodium hydride in 70 ml of N,N-dimethylformamide is heated at 50° C. for 30 minutes then cooled. A solution of 2.22 g of 1-bromo-4-cyano-butane in 25 ml of N,N-dimethylformamide is added dropwise to the reaction mixture and stirring continued for 3 hours. The reaction mixture is quenched in 400 ml of ice water and extracted with (2×300 ml) of ethyl acetate. The organic layer is dried with magnesium sulfate and evaporated to afford a solid which is stirred with ether, filtered and dried to yield 2.5 g of the desired product as a solid, m.p. 120°–122° C.

EXAMPLE 9

6-(Butylthio)-benz[cd]indol-2(1H)-one

A stirred solution of 1.8 g of 1,2-dihydro-2-oxobenz[cd]indol-6-yl-thiocyanic acid ester (Example 1) in 40 ml of ethanol is treated with 1 g of sodium borohydride over 1 hour followed by the rapid addition of 1.8 g of iodobutane. The reaction mixture is stirred at room temperature for 1 hour then rapidly brought to a boil, the heat removed and stirred at room temperature for 1 hour. The reaction mixture is poured over crushed ice and stirred for 20 minutes and the solid collected and washed with water. The solid is dried at 56° C. under vacuum to yield 1.8 g of the desired product as yellow solid, m.p. 126°–129° C.

EXAMPLE 10

6-[(1-Methylethyl)thio]1-benz[cd]indol-2(1H)-one

A mixture of 1.8 g of 1,2-dihydro-2-oxobenz-[cd]indol-6-yl-thiocyanic acid ester (Example 1), 1 g of sodium borohydride and 0.9 ml of 2-bromopropane in 40 ml of ethanol are reacted as described in Example 9 giving 1.7 g of the desired product as a yellow solid, m.p. 180°–184° C.

EXAMPLE 11

1-Ethyl-6-(methylsulfonyl)-benz[cd]indol-2(1H)-one

To 25 ml of N,N-dimethylformamide is added 0.48 g of 60% sodium hydride followed by the dropwise addition of a solution of 1.976 g of 6-(methylsulfonyl)-benz[cd]indol-2(1H)-one (Example 3) in 50 ml of N,N-dimethylformamide. Stirring is continued for 20 minutes followed by heating at 50° C. for 10 minutes then cooling at room temperature. A solution of 1.872 g of ethyl iodide in 25 ml of N,N-dimethylformamide is added dropwise and stirring continued for 1.5 hours. The reaction mixture is poured over cracked ice and the solid collected, dried and crystallized from ethyl acetate to give 1.03 g of the desired product as a solid, m.p. 199°–203° C.

EXAMPLE 12

6-(Ethylthio)-benz[cd]indol-2(1H)-one

A mixture of 1.2 g of 1,2-dihydro-2-oxobenz[cd]indol-6-yl-thiocyanic acid ester (Example 1), 0.66 g of sodium borohydride and 0.5 ml of ethyl iodide in 30 ml of ethyl alcohol are reacted as described in Example 9 giving 1 g of the desired product as a yellow solid, m.p. 144°–146° C.

EXAMPLE 13

6-(Propylthio)-benz[cd]indol-2(1H)-one

A mixture of 1.8 g of 1,2-dihydro-2-oxobenz[cd]indol-6-yl-thiocyanic acid ester (Example 1), 1 g of sodium borohydride and 0.9 ml of 1-bromopropane in 40 ml of ethyl alcohol are reacted as described in Example 9 giving 1.8 g of the desired product, m.p. 145°–148° C.

EXAMPLE 14

1-Acetyl-6-(methylthio)-benz[cd]indol-2-(1H)-one

A mixture of 1 g of 6-(methylthio)-benz[cd]-indol-2(1H)-one (Example 2) and 10 ml of acetic anhydride is stirred and heated at reflux for 2 hours, cooled and filtered. The cake is washed with ethanol and ether then dried. The dried cake is suspended in 15 ml of hot ethanol, filtered and the cake crystallized from 150 ml of ethanol to afford the desired product as a solid.

EXAMPLE 15

6-(Methylsulfinyl)-benz[cd]indol-2(1H)-one

To an ice water cooled stirred suspension of 1.3 g of 6-(methylthio)-benz[cd]indol-2(1H)-one (Example 2) in 25 ml of ethanol is added portionwise over 12 minutes 1.2 g of 85% m-chloroperbenzoic acid at a rate so the temperature is kept below 7° C. Stirring is continued over 1.25 hours. The reaction mixture is poured over crushed ice and 8 ml of 1N sodium hydroxide with stirring. After 15 minutes of additional stirring, the reaction mixture is filtered. The filtrate is extracted with methylene chloride, dried with magnesium sulfate and evaporated to afford 0.65 g of the desired product as a yellow solid, m.p. 178°–185° C.

EXAMPLE 16

1,2-Dihydro-1-methyl-2-oxobenz[cd]indol-6-ylthiocyanic acid ester

A mixture of 4.66 g of 1,2-dihydro-2-oxobenz-[cd]indol-6-yl-thiocyanic acid ester (Example 1) in 125 ml of N,N-dimethylformamide and 1.24 g of 60% sodium hydride is stirred at room temperature for 30 minutes. Added dropwise is 4.39 g of methyl iodide followed by stirring for 2 hours. The reaction mixture is poured over 500 ml of ice water and extracted with ethyl acetate. The organic layer is dried with magnesium sulfate and evaporated to a residue which is stirred with acetone and filtered to afford 2.58 g of the desired product as a solid, m.p. 147°–153° C.

EXAMPLE 17

6-[[(Acetyloxy)methyl]thio]benz[cd]indol-2(1H)-one

A stirred solution of 1.8 g of 1,2-dihydro-2-oxobenz[cd]indol-6-yl-thiocyanic acid ester (Example 1) in 40 ml of ethyl alcohol is treated with 1 g of sodium borohydride over 1 hour followed by the rapid addition of 1.5 g of bromomethylacetate. After stirring for 30 minutes, the reaction mixture is poured over crushed ice and the solid collected and dried to afford 1.7 g of yellow solid which is dissolved in 60 ml of methylene chloride, filtered and the filtrate evaporated to give 1.2 g of the desired product as a yellow solid, m.p. 149°–154° C.

EXAMPLE 18

6-(Ethylsulfonyl)-benz[cd]indol-2(1H)-one

A mixture of 1 g of 6-(ethylthio)-benz[cd]indol-2(1H)-one (Example 12) and 1.8 ml of 30% hydrogen peroxide in 11 ml of glacial acetic acid is heated at reflux for 20 minutes. Crystals form upon cooling and are collected. The solid is washed with acetic acid followed by water then vacuum dried to afford 0.9 g of the desired product, m.p. 270°–272° C.

EXAMPLE 19

1-Butyl-6-(methylthio)-benz[cd]indol-2(1H)-one

A mixture of 2.15 g of 6-(methylthio)-benz[cd]indol-2(1H)-one (Example 12), 0.6 g of 60% sodium hydride and 1.7 ml of butyl iodide in 70 ml are reacted as described in Example 16 giving 1.85 g of the desired product as a solid, m.p. 75°–77° C.

EXAMPLE 20

1-Methyl-6-(thiomethyl)-benz[cd]indol-2(1H)-one

A mixture of 1.07 g of 6-(methylthio)-benz[cd]indol-2(1H)-one (Example 12), 300 mg of 60% sodium hydride and 0.5 ml of methyl iodide in 50 ml of N,N-dimethylformamide are reacted as described in Example 16 giving 0.65 g of the desired product, m.p. 84°–85° C.

We claim:

1. A method of meliorating hypertensive conditions in a mammal which comprises administering to said mammal an effective amount of a compound of the formula:

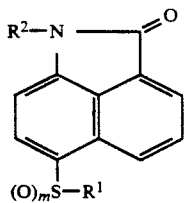

wherein
R[1] is selected from the group consisting of lower alkyl ($C_1$–$C_4$) branched or unbranched, —CN and —CH$_2$OCOR[3] wherein R[3] is selected from $C_1$–$C_3$ alkyl branched or unbranched; R[2] is selected from the group consisting of hydrogen, lower alkyl ($C_1$–$C_4$) branched or unbranched, —(CH$_2$)$_q$CN, —(CH$_2$)$_q$-cyclopropyl and —COR[3] wherein R[3] is selected from $C_1$–$C_3$ alkyl branched or unbranched; m is an integer from 0 to 2 and q is an integer from 1 to 3; with the proviso that when R[1] is CN, m is 0.

2. A method according to claim 1 wherein R[1] is selected from the group consisting of lower alkyl ($C_1$–$C_4$) branched or unbranched, —CN and —CH$_2$OCOCH$_3$ and R[2] is selected from the group consisting of hydrogen, lower alkyl ($C_1$–$C_4$) branched or unbranched, —(CH$_2$)$_3$CN, —(CH$_2$)-cyclopropyl and —COCH$_3$.

3. A method according to claim 1 wherein R[1] is selected from —CN and —CH$_2$OCOCH$_3$ and R[2] is selected from —(CH$_2$)$_3$CN, —CH$_3$-cyclopropyl and —COCH$_3$.

4. A method according to claim 1 wherein the compound is 6-(methylthio)-benz[cd]indol-2(1H)-one.

5. A method according to claim 1 wherein the compound is 6-(methylsulfonyl)-benz[cd]indol-2(1H)-one.

6. A method according to claim 1 wherein the compound is 1-methyl-6-(methylsulfonyl)-benz[cd]indol2(1H)-one.

7. A method according to claim 1 wherein the compound is 1-(1-methylethyl)-6-(methylsulfonyl)benz[cd]indol-2(1H)-one.

8. A method according to claim 1 wherein the compound is 1-(1-methylethyl)-6-(methylthio)-benz[cd]indol-2(1H)-one.

9. A method according to claim 1 wherein the compound is 1-(cyclopropylmethyl)-6-(methylsulfonyl)-benz[cd]-indol-2(1H)-one.

10. A method according to claim 1 wherein the compound is 6-(methylthio)-2-oxo-benz[cd]indole-1(2H)-butanenitrile.

11. A method according to claim 1 wherein the compound is 6-(butylthio)-benz[cd]indol-2(1H)-one.

12. A method according to claim 1 wherein the compound is 6-[(1-methylethyl)thio]-benz[cd]indol2(1H)-one.

13. A method according to claim 1 wherein the compound is 1-ethyl-6-(methylsulfonyl)-benz[cd]indol-2(1H)-one.

14. A method according to claim 1 wherein the compound is 6-(ethylthio)-benz[cd]indol-2(1H)-one.

15. A method according to claim 1 wherein the compound is 6-(propylthio)-benz[cd]indol-2(1H)-one.

16. A method according to claim 1 wherein the compound is 6- ethylsulfonyl)-benz[cd]indol-2(1H)-one.

17. A method according to claim 1 wherein the compound is 1-butyl-6-(methylthio)-benz[cd]indol-2(1H)-one.

18. A method according to claim 1 wherein the compound is 1-methyl-6-(thiomethyl)-benz[cd]indol-2(1H)-one.

19. A method according to claim 1 wherein the compound is 1,2-dihydro-2-oxobenz[cd]indol-6-yl-thiocyanic acid ester.

20. A method according to claim 1 wherein the compound is 1-acetyl-6-(methylthio)-benz[cd]indol-2-(1H)-one.

21. A method according to claim 1 wherein the compound is 6-(methylsulfinyl)-benz[cd]indol-2(1H)-one. 2-oxo-benz[cd]indole-2(1H)-one.

22. A method according to claim 1 wherein the compound is 1,2-dihydro-1-methyl-2-oxobenz[cd]indol-6-yl-thiocyanic acid ester.

23. A method according to claim 1 wherein the compound is 6-[[(acetyloxy)methyl]thio]benz[cd]indol-2(1H)-one.

24. A compound selected from:
6-(methylthio)-2-oxo-benz[cd]indole-1(2H)-butanenitrile;
1,2-dihydro-2-oxobenz[cd]indol-6-yl-thiocyanic acid ester;
1-acetyl-6-(methylthio)-benz[cd]indol-2-(1H)-one;
1,2-dihydro-1-methyl-2-oxobenz[cd]indol-6-yl-thiocyanic acid ester; or
6-[[(acetyloxy)methyl]thio]benz[cd]indol-2(1H)-one.

25. The compound of claim 24, 6-(methylthio)2-oxobenz[cd]indole-1(2H)-butanenitrile.

26. The compound of claim 24, 1,2-dihydro-2-oxobenz[cd]indol-6-yl-thiocyanic acid ester.

27. The compound of claim 24, 1-acetyl-6-(methylthio)-benz[cd]indol-2-(1H)-one.

28. The compound of claim 24, 1,2-dihydro-1-methyl-2-oxobenz[cd]indol-6-yl-thiocyanic acid ester.

29. The compound of claim 24, 6-[[(acetyloxy)methyl]thio]benz[cd]indol-2(1H)-one.

30. The compound 6-(methylsulfinyl)-benz[cd]indol-2(1H)-one.

* * * * *